(12) United States Patent
Alenad et al.

(10) Patent No.: US 9,345,734 B2
(45) Date of Patent: May 24, 2016

(54) ACHILLEA FRAGRANTISSIMA EXTRACT, METHOD FOR PREPARING ACHILLEA FRAGRANTISSIMA EXTRACT AND METHOD FOR TREATING CHRONIC MYELOID LEUKEMIA

(71) Applicant: King Saud University, Riyadh (SA)

(72) Inventors: Asma Majed Alenad, Riyadh (SA); Nabila Abdul-Aziz Al-Jaber, Riyadh (SA)

(73) Assignee: King Saud University, Riyadh (SA)

( * ) Notice: Subject to any disclaimer, the term of this patent is extended or adjusted under 35 U.S.C. 154(b) by 377 days.

(21) Appl. No.: 13/868,427

(22) Filed: Apr. 23, 2013

(65) Prior Publication Data
US 2014/0314886 A1 Oct. 23, 2014

(51) Int. Cl.
*A61K 36/28* (2006.01)

(52) U.S. Cl.
CPC ............. *A61K 36/28* (2013.01); *A61K 2236/00* (2013.01)

(58) Field of Classification Search
CPC ..................................................... A61K 36/28
USPC ....................................................... 424/725
See application file for complete search history.

(56) References Cited

U.S. PATENT DOCUMENTS

| | | | |
|---|---|---|---|
| 7,022,350 B2 | 4/2006 | Harvey et al. | |
| 7,172,774 B2 | 2/2007 | Leko | |
| 7,615,574 B2 | 11/2009 | Bandyopadhyay et al. | |
| 7,964,221 B2 | 6/2011 | Pylypchuk | |
| 2004/0091558 A1 | 5/2004 | Lutz et al. | |
| 2009/0175966 A1* | 7/2009 | Lutz et al. | 424/739 |
| 2009/0191289 A1* | 7/2009 | Lutz et al. | 424/739 |
| 2014/0096485 A1* | 4/2014 | Malallah | 53/435 |

FOREIGN PATENT DOCUMENTS

NZ 575241 A 10/2010

OTHER PUBLICATIONS

Alkofahi et al. Int. J. Crude Drug Res. 1990. vol. 28, No. 2, pp. 139-144.*
Hamed et al. Revista de Fitoterapia. Sep. 2010. vol. 10, Suppl. 1, p. 119, Abstract Number: ISE5-P06. EMBASE Abstract enclosed.*
Thoppil et al. Pharmaceutical Biol. 2013. vol. 51, No. 5, pp. 668-674.*
Alenad et al. J. Medicinal Plants Res. Jun. 2013. vol. 7, No. 21, pp. 1561-1567.*
Sathiyamoorthy, P. et al., "Larvicidal Activity in Desert Plants of the Negev and Bedouin Market Plant Products," Phytochemical Society of North America, vol. 35, No. 4, 1997, pp. 265-273.
Meshkini, A. et al., "Induction of Megakaryocytic Differentiation in Chronic Myelogenous Leukemia Cell K562 by 3-Hydrogenkwadaphnin," Journal of Biochemistry and Molecular Biology, vol. 40, No. 6, 2007, pp. 944-951.
Tarawneh, K.A. et al., "Evaluation of Antibacterial and Antioxidant Activities of Methanolic Extracts of Some Medicinal Plants in Northern Part of Jordan," Journal of Biological Sciences, vol. 10, No. 4, 2010, pp. 325-332.
Al-Mustafa, A.H. et al., "Antioxidant Activity of Some Jordanian Medicinal Plants Used Traditionally for Treatment of Diabetes," Pakistan Journal of Biological Sciences, vol. 11, No. 3, 2008, pp. 351-358.
Elmann, A. et al., "Anti-Neuroinflammatory effects of the extract of Achillea fragrantissima," BMC Complementary and Alternative Medicine, vol. 11:98, 2011, pp. 1-10.
Rosson, D. et al., "Constitutive c-myb Expression in K562 Cells Inhibits Induced Erythroid Differentiation but Not Tetradecanoyl Phorbol Acetate-Induced Megakaryocytic Differentiation," Molecular and Cellular Biology, vol. 15, No. 2, 1995, pp. 772-779.
Al-Mustafa, A.H., "Antioxidant Activity of Some Jordanian Medicinal Plants Used Traditionally for Treatment of Diabetes," Pakistan Journal of Biological Sciences, vol. 11, 2008, pp. 351-358.
Pettersson, F. et al., "The 12th international conference on differentiation therapy: targeting the aberrant growth, differentiation and cell death programs of cancer cells," Cell Death and Differentiation, vol. 18, 2011, pp. 1231-1233.
Assouline, S. et al., "Monitoring response and resistance to treatment in chronic myeloid leukemia," Current Oncology, vol. 18, No. 2, 2011, pp. 82-94.
Santoro, M. et al., "RET: A Multi-Faceted Gene in Human Cancer," Endocrinol Metab, vol. 27, No. 3, 2012, pp. 173-179.
Miao, S. et al., "Proliferation-Attenuating and Apoptosis-Inducing Effects of Tryptanthrin on Human Chronic Myeloid Leukemia K562 Cell Line in Vitro," International Journal of Molecular Sciences, vol. 12, 2011, pp. 3831-3845.
Apperley, J., "Part I: Mechanisms of resistance to imatinib in chronic myeloid leukaemia," Lancet Oncology, vol. 8, 2007, pp. 1018-1029.
McGee, M.M. et al., "Pyrrolo-1,5-benzoxazepines Induce Apoptosis in Chronic Myelogenous Leukemia (CML) Cells by Bypassing the Apoptotic Suppressor Bcr-Abl," The Journal of Pharmacology and Experimental Therapeutics, vol. 296, No. 1, 2001, pp. 31-40.
Vaidya, S. et al., "Recent developments in drug resistance mechanism in chronic myeloid leukemia: a review," European Journal of Haematology, vol. 87, 2011, pp. 381-392.
Hegde, S. et al., "Stat3 promotes the development of erythroleukemia by inducing Pu. 1 expression and inhibiting erythroid differentiation," Oncogene, vol. 28, No. 38, 2009, pp. 3349-3359.

(Continued)

*Primary Examiner* — Chris R Tate
(74) *Attorney, Agent, or Firm* — Hauptman Ham, LLP (57) ABSTRACT

An *Achillea fragrantissima* extract for treating chronic myeloid leukemia cells is made by the following steps: washing a mass of *Achillea fragrantissima* leaves and powdering the dried leaves. The leaves are dried over seven days and a kilo of the powder is extracted three times with methanol. The resulting material is concentrated and redissolved in water to form a concentration of 0.5 mg/mL and centrifuged to remove any undissolved material. The final *Achillea fragrantissima* extract may then be used to cause morphological changes in CML cells and treat humans with chronic myeloid leukemia.

8 Claims, 8 Drawing Sheets

(56) References Cited

OTHER PUBLICATIONS

Hallock, S. et al., "Aurintricarboxylic Acid Inhibits Protein Synthesis Independent, Sanguinarine-Induced Apoptosis and Oncosis," Toxicologic Pathology, vol. 35, 2007, pp. 300-309.

Subhashini, J. et al., "Molecular mechanisms in C-Phycocyanin induced apoptosis in human chronic myeloid leukemia cell line-K562," Biochemical Pharmacology, vol. 68, 2004, pp. 453-462.

Jin, U.H. et al., "Membrane type sialidase inhibits the megakaryocytic differentiation of human leukemia K562 cells," Biochimica et Biophysica Acta, vol. 1780, 2008, pp. 757-763.

Soltan, M.M. et al., "Antiviral screening of forty-two Egyptian medicinal plants," Journal of Ethnopharmacology, vol. 126, 2009, pp. 102-107.

Yaniv, Z. et al., "Plants Used for the Treatment of Diabetes in Israel," Journal of Ethnopharmacology, vol. 19, 1987, pp. 145-151.

Strober, W., "Trypan Blue Exclusion Test of Cell Viability," Current Protocols in Immunology, 1997, pp. A.3B.1-A.3B.2.

Leszczyniecka, M. et al., "Differentiation therapy of human cancer: basic science and clinical applications," Pharmacology & Therapeutics, vol. 90, 2001, pp. 105-156.

\* cited by examiner

*Achillea fragrantissima* extract inhibits K562 cell proliferation.

FIG. 4

Death of K562 cells following incubation with *Achillea fragrantissima* methanol extract.

ACHILLEA FRAGRANTISSIMA EXTRACT, METHOD FOR PREPARING ACHILLEA FRAGRANTISSIMA EXTRACT AND METHOD FOR TREATING CHRONIC MYELOID LEUKEMIA

FIELD OF THE INVENTION

This invention relates to a method for inhibiting growth and promoting mortality of chronic myeloid leukemia cells, and *Achillea fragrantissima* extract for inhibiting growth and promoting mortality in chronic myeloid leukemia cells and to a method for treating mammals, primarily human beings with chronic myeloid leukemia.

BACKGROUND FOR THE INVENTION

Herbs with medicinal properties have regained worldwide attention due to their therapeutic effect in the treatment of many chronic diseases. The advantages of herbs are due to their non-toxic nature and specificity to aberrantly expressed molecules. Many of the beneficial effects arise from the antioxidant components of herbs. For example, *Achillea fragrantissima* has been used to treat viral fever, arthritis and diabetes in the Middle East. In a recent study by Applicant, anticancer properties of extracts from *Achillea fragrantissima* plant were tested using chronic myeloid leukemia (CML) cell line K562. *Achillea fragrantissima* extract induced differentiation, inhibited growth and brought about death of K562 cells in a time and concentration dependent manner. Differentiation of K562 cells was associated with clearly identifiable morphological change from a round to a spindle shape. *Achillea fragrantissima* extract also caused disintegration of K562 cell membrane. Induction of cellular differentiation was followed by terminal maturation and eventual death.

Genetic changes involving DNA rearrangements in pluripotent hematopoietic stem cells inhibit differentiation and result in accumulation of undifferentiated erythropoietic cells in blood (1). CML cells in 95% of patients possess Philadelphia chromosome, a genetic rearrangement resulting from reciprocal translocation between chromosome 9 and 22 involving BCR-ABL (Copland et al., 2005). Every year approximately 5000 new cases of CML are diagnosed in the US. CML is now treated with tyrosine kinase inhibitors (TKIs), such as imatinib, dasatinib, or nilotinib.

Discovery of imatinib (also known as Gleevec), a specific BCR-ABL kinase inhibitor, for the treatment of CML in the late 1990s was considered a medical milestone and since has dramatically improved survival rates (2). Imatinib is highly effective in treating the early stages of chronic myeloid leukemia, but remission induced in advanced phase have been shown to reduce survival (3). A third of patients failed to achieve the desired effect with imatinib and hence were considered resistant (4, 5). The primary cause of imatinib resistance in CML patients was thought to be the mutations in the BCR/ABL kinase domain, clonal evolution and amplification of the BCR-ABL gene (4, 6). T315I mutation of the BCR/ABL tyrosine kinase accounts for 10-15% of clinically relevant CML mutations and licensed tyrosine kinase inhibitors are ineffective against this mutation reduces life expectancy of CML in chronic phase from 10 years to just 22 months (7).

Up to now, there has been considerable focus on the role of ABL-kinase-domain mutations as mediators of resistance to imatinib, thereby encouraging the development of a second generation of TKIs capable of inhibiting these mutant proteins. However, increasingly studies have shown that the mutations do not account for all cases of resistance and have a negligible role in the inability of TKIs to eradicate residual disease in patients who are good responders. More recently, attention has turned to the relative roles of drug bioavailability and drug efflux and drug influx proteins in the development of resistance to imatinib (6). Recent history shows that cancer treatments using small molecule inhibitors targeting specific tyrosine kinases eventually lead to development of resistance by cancer cells.

Thus to overcome drug resistance and relapse of disease, therapy with minimal side effects is highly demanded in the clinical field. In that respect, differentiation induction therapy has attracted universal attention (Koeffler, 1983; Spira and Carducci, 2003).

Differentiation therapy is an alternative approach to CML treatment due to its higher specificity compared to the traditional approaches with cytotoxic drugs (Sell, 2006). The human CML K562 cell line established from pleural effusion of a patient in blast crisis (Lozzio and Lozzio, 1977) has been extensively used as an in vitro model for studying differentiation potential of many compounds (Koeffler and Golde, 1980).

Several differentiation inducing agents such as hemin (Villeval et al., 1983), daunomycin (Tonni et al., 1987), herbimycin A (Honma et al., 1989), phorbol esters (phorbol dibutyrate and phorbol 12-myristate 13-acetate, PMA) (Tetteroo et al., 1984; Alitalo, 1990) and thrombopoietin (TPO) (Rouyez et al., 1997) have been used to induce the erythroid differentiation of K562 cell line. Regardless of these achievements, clinical evaluations of these compounds have not been promising. For instance, clinical use of PMA is not recommended due to its tumor-promoting activity. Thus, universal efforts have been devoted to find new and potent differentiation inducers devoid of general toxicities.

For the above reasons, plants have been the center of focus as a natural source for obtaining novel antioxidant, antivenom, antifungal, antibacterial and anti leukemic Activity agents with differentiation capability (Shu, 1998). Among plant-derived agents, the daphnane-type diterpene esters such as genkwadaphnin (Yazdanparast and Sadeghi, 2004), genididin, geniditrin and gnidilatin (Stanoeva et al., 2005) possess significant antileukemic activities with major metabolic effects on DNA and protein syntheses (8).

The genus *Achillea* consisting of about 140 perennial herbs has traditionally been used to treat digestive problems, liver and gall-bladder conditions, menstrual irregularities, cramps, fever, wound healing among others. Recent findings have confirmed several traditional uses on the analgesic, anti-ulcer, choleretic, hepatoprotective and wound healing activities. Of these, *A. fragrantissima* species has been used as traditional medicine by Middle East countries (9-11). *A. fragrantissima* extract was shown to possess antiviral activity against herpes simplex-1 virus (HSV), poliomyelitis-1 virus (POLIO) and vesicular stomatitis virus (VSV) (12). Powerful antineuroinflammatory functions of *A. fragrantissima* extract have been reported recently (13). Mechanistically, strong antioxidant potential of *A. fragrantissima* extract has been suggested to be responsible for its antibacterial action (14).

In this study Applicant evaluated the anticancer properties of *Achillea fragrantissima* extract on human CML cell line K562. Applicant's results indicated that *Achillea fragrantissima* extract can induce differentiation, cell maturation and apoptosis of K562 cells and hence may serve as a safe and effective therapeutic in the treatment of CML.

SUMMARY OF THE INVENTION

In essence, the present invention contemplates a method for preparing *Achillea fragrantissima* extract for inhibiting growth and promoting mortality of chronic myeloid leukemia cells. The method comprises or consists of the following steps. In a first step, a mass of *Achillea fragrantissima* leaves are provided and washed to remove dirt. The washed leaves are then dried at room temperature for seven days and powdered in a second step. In a third step one kilogram of powdered leaves are extracted three times with methanol under reflux followed by a fourth step of concentrating the powdered *Achillea fragrantissima* extract to dryness in a rotary evaporator under reduced pressure at 35° C. over anhydrous sodium sulfate. Then about 100 mg of dried *Achillea fragrantissima* extract was redissolved in about 200 uL of water to form a solution with a final concentration of 0.5 mg/mL in a fifth step. Then finally in a sixth step centrifuge to remove any undissolved matter and leave a supernatant *Achillea fragrantissima* extract for inhibiting cell growth and leading to cell mortality of chronic myeloid leukemia cells.

In a preferred embodiment of the invention, the supernatant *Achillea fragrantissima* extract is used to treat chronic myeloid leukemia cells. For example, in a first step, a sample of chronic myeloid leukemia cells are introduced into a RPMI (Rosewell Park Memorial Institute) 1640 culture media supplemented with 10% fetal bovine serum, streptomycin (100 μg/mL) and penicillin (100 U/mL) (Sample A) plus in the final steps, $5 \times 10^4$ cells/mL were distributed into 24 well plates (1 mL/well) and incubated under 5% $CO_2$ in a humidified atmosphere at 37° C. and the cell mortality evaluated after 16 hours after the addition of the *Achillea fragrantissima* (Sample A).

Following the above, an initial dosage for a human being is determined and given to a patient.

*A. fragrantissima* extract induced death of K562 cells in a dose- and time-dependent manner.

Figure 1:
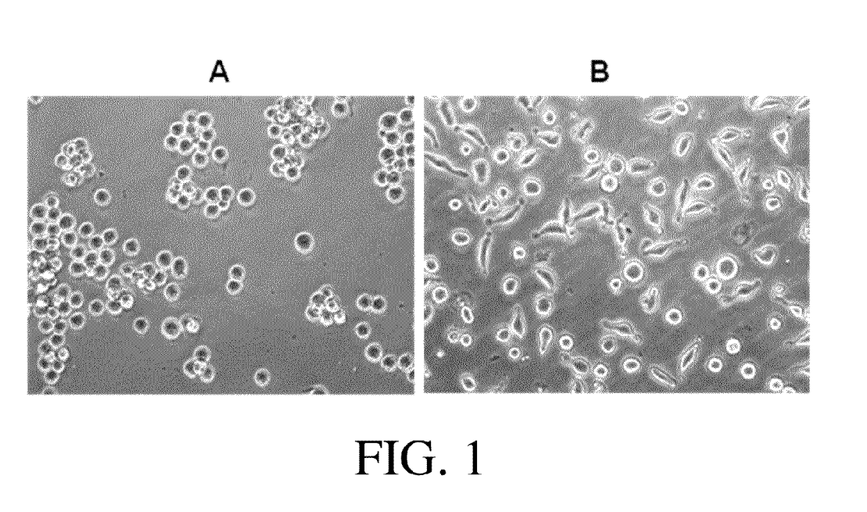
FIG. 1 is an *Achillea fragrantissima* methanol extract induced morphological alterations in K562 cells. A. K562 cells in RPMI medium were incubated overnight (16 h) without *Achillea fragrantissima* methanol extract (0.5 mg/mL), B. K562 cells in RPMI medium were incubated overnight (16 h) with *Achillea fragrantissima* methanol extract (0.5 mg/mL). Pictures of cells in flasks were taken using an inverted light microscope.
Figure 2:
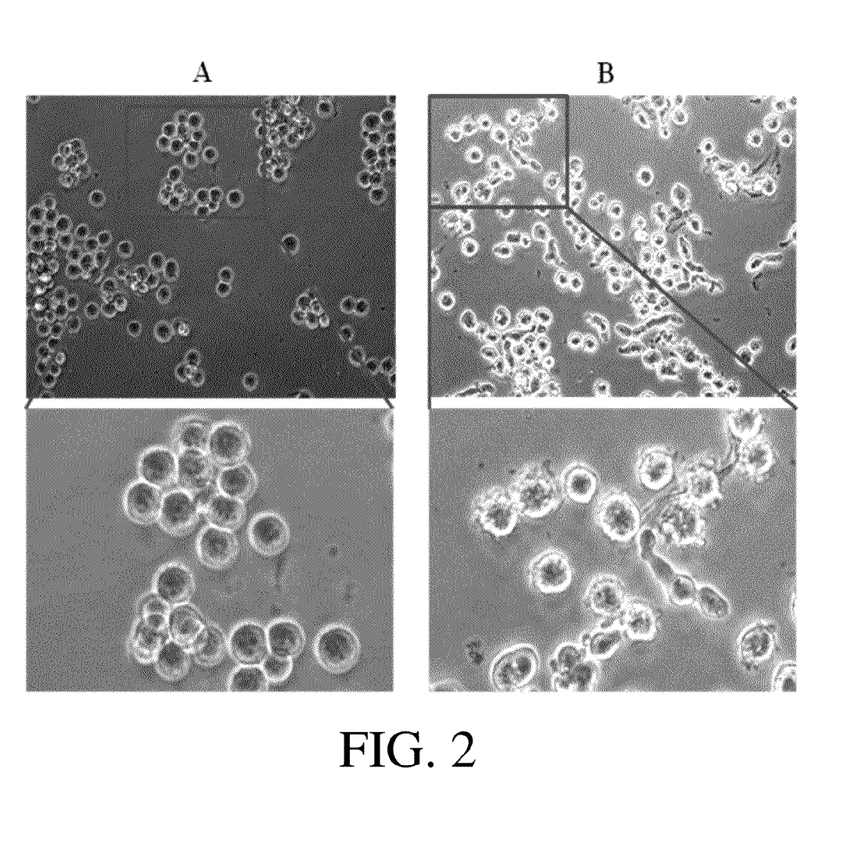
FIG. 2 is a close-up images of K562 cell undergoing blabbing and membrane disintegration following incubation with *Achillea fragrantissima* extract. A. K562 cells in RPMI medium without *Achillea fragrantissima* extract, B. K562 cells in RPMI with *Achillea fragrantissima* extract (1 mg/ml)

At a low concentration of 0.5 mg/mL *A. fragrantissima* extract inhibited the cell growth while the control cells grew exponentially in Applicants' observations over a 3 day period (FIG. 1). *A. fragrantissima* extract inhibited growth from 0.1 mg/mL concentration and level of inhibition increased with increasing concentration of the extract (FIG. 2). From concentrations above 1 mg/mL death of cells was seen just after 24 h. Death of most of the cells occurred at 48 h at 2 and 4 mg/mL concentrations.

K562 cells in RPMI medium were incubated overnight (16 h) without (A) or with (B) crude extract from *A. fragrantissima* (0.5 mg/mL) (Sample B). Pictures of cells in flasks were taken using an inverted light microscope.

Close-up images of K562 cells undergoing blebbing and membrane disintegration following incubation with *A. fragrantissima* extract. K562 cells in RPMI medium (A); K562 cells in RPMI+*A. fragrantissima* extract (1 mg/mL).

In a further embodiment of the invention, an *Achillea fragrantissima* extract for inhibiting growth and leading to the mortality of chronic myeloid leukemia cells are produced by the above-described method.

In a still further embodiment of the invention, a method for treating chronic myeloid leukemia in a mammal and particularly in a human being includes the steps of administering a pharmaceutical composition consisting essentially of a pharmaceutically effective *Achillea fragrantissima* extract to obtain growth inhibition and cell mortality of chronic myeloid leukemia cells with streptomycin (100 μg/mL) and penicillin (100 U/mL).

The invention will now be described in connection with the following figures.

DESCRIPTION OF THE DRAWINGS

FIGS. 5(*a-f*) shows the effect of different TLC & CC isolated compounds (P1-P5) of *Achillea fragrantissima* ether extract bring about the same morphological change in K562 cells.

DESCRIPTION OF THE PREFERRED EMBODIMENTS OF THE INVENTION

*Achillea fragrantissima* is a desert flowering plant with common names, lavender cotton (English), qayeum (Arabic)

etc. It has been described as a fragrant chamaethyte, 50-100 cm, many stemmed from a woody base into small oblong ovait leaves.

The *Achillea fragrantissima* extract is presently being considered for use in a method for inhibiting growth and promoting mortality of chronic myeloid leukemia cells.

Materials

The cell culture medium (RPMI-1640), fetal bovine serum (FBS) and penicillin-streptomycin were purchased from Gibco BRL (Life technology). The K562 cell line derived originally from CML patient in blast crisis was obtained from American Type Culture Collection (ATCC), USA.

Methods

*A. fragrantissima* Extract Preparation

*Achillea fragrantissima* leaves were washed to remove dirt, allowed to dry at room temperature for 7 days and finely powdered. 1 kg of powder was extracted thrice with methanol under reflux. The extract was concentrated to dryness in rotary evaporator under reduced pressure at >35° C. and dried over anhydrous sodium sulphate. 100 mg of dried *Achillea fragrantissima* extract was redissolved in 200 uL of water to yield a solution with a final concentration of 0.5 mg/mL, centrifuged to remove any undissolved material and the supernatant used for treating cells.

Cell Culture

The human K562 cell line was cultured in RPMI-1640 medium supplemented with fetal bovine serum (FBS) (10%, v/v), streptomycin (100 µg/mL) and penicillin (100 U/mL). $5 \times 10^4$ cells/mL were distributed into 24 well plates (1 mL/well) and incubated under 5% $CO_2$ in a humidified atmosphere at 37° C. 24 h after incubation, when the cells were ~20% confluent, appropriate concentrations of *Achillea fragrantissima* extracts were added from the aqueous stock solution of 0.5 mg/mL. Incubations were continued for various durations and at the end cells were counted by trypan blue method.

Cell Viability Assay

Cell numbers and viabilities were assessed using a hemocytometer based on the ability of the viable cells to exclude trypan blue (15).

Morphological Evaluation of Differentiated Cells

Pictures of *Achillea fragrantissima* treated and control cells were taken after 24 h using an inverted light microscope. Differentiated K562 cells were identified on the basis of morphological changes as described previously (16).

Results

Effect of *Achillea fragrantissima* Extract on K562 Cell Morphology

*Achillea fragrantissima* extract was added at various concentrations into cells grown in RPMI medium containing 10% FBS and penicillin and streptomycin antibiotics. Initial studies revealed significant morphological changes in K562 cells and hence further studies were pursued with these cells.

*Achillea fragrantissima* extract altered the morphology of K562 cells. The effect was more pronounced at 0.5 mg/mL. Morphological changes involve alteration from the original spherical to elliptical shapes (FIG. 1). At concentrations of 1 mg/mL cells were more elongated and seem to indicate cell cycle arrest (FIG. 2). At concentration >1 mg/mL disintegration of membrane and cell death seem to predominate rather than shape change. Up to 30% of cells were morphologically altered at 16 h after addition of *Achillea fragrantissima* extract. The morphological changes were found to be good predicators of future cell death.

Effect of *Achillea fragrantissima* Extract on Cell Viability

*Achillea fragrantissima* extract induced death of K562 cells in a dose- and time-dependent manner. At a low concentration of 0.5 mg/mL *Achillea fragrantissima* extract inhibited the cell growth while the control cells grew exponentially in our observations over a 3 day period (FIG. 3). *Achillea fragrantissima* extract inhibited growth from 0.1 mg/mL concentration and level of inhibition increased with increasing concentration of the extract (FIG. 4). From concentrations above 1 mg/mL death of cells was seen just after 24 h. Death of most of the cells occurred at 48 h at 2 and 4 mg/mL concentrations.

FIG. 1. *Achillea fragrantissima* extract induced morphological alterations in K562 cells. K562 cells in RPMI medium were incubated overnight (16 h) without (A) or with (B) crude extract from *A. fragrantissima* (0.5 mg/mL). Pictures of cells in flasks were taken using an inverted light microscope.

FIG. 2. K562 cell membrane disintegration. Close-up images of K562 cells undergoing blebbing and membrane disintegration following incubation with *Achillea fragrantissima* extract. K562 cells in RPMI medium (A); K562 cells in RPMI+*Achillea fragrantissima* extract (1 mg/mL).

Figure 3:
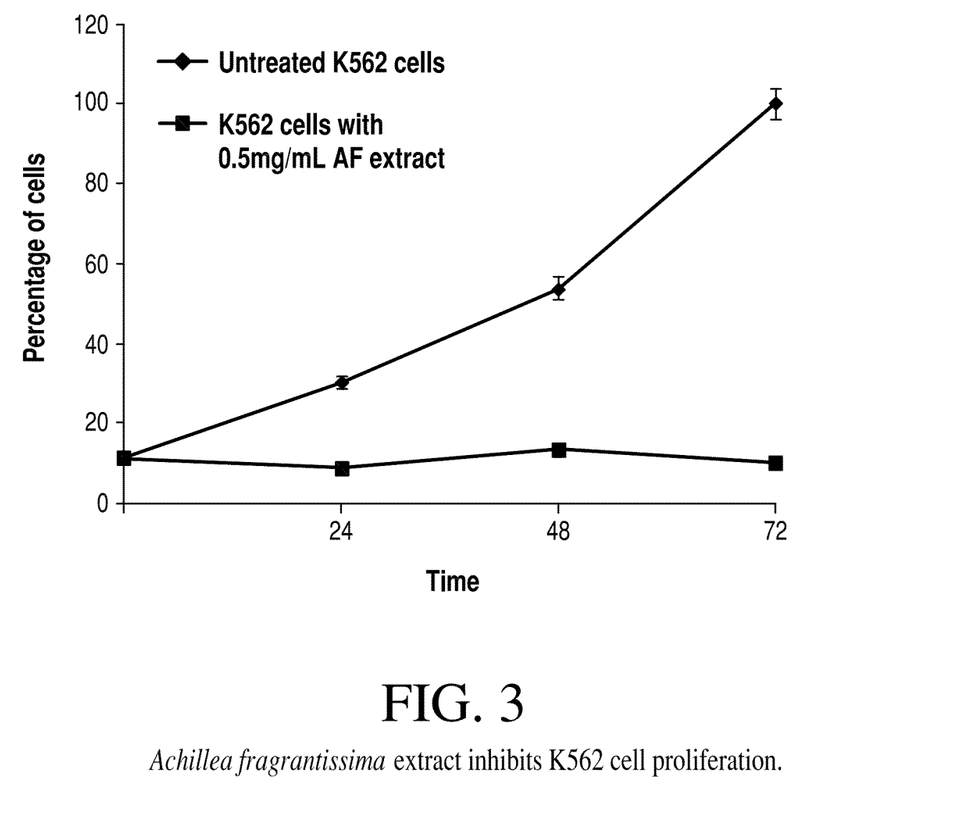
FIG. 3 is an *Achillea fragrantissima* extract inhibits K562 cell proliferation; K562 cells incubated with 0.5 mg/ml of *Achillea fragrantissima* methanol extract were followed for 72 h for cell growth. Viable cells were determined by trypan blue assay. *Achillea fragrantissima* extract inhibited the proliferation completely while the control cells grew exponentially during this period. Cell numbers with SD were averaged from 3 independent experiments. Number of untreated cells at the end of the incubation period was considered 100%.
Figure 4:
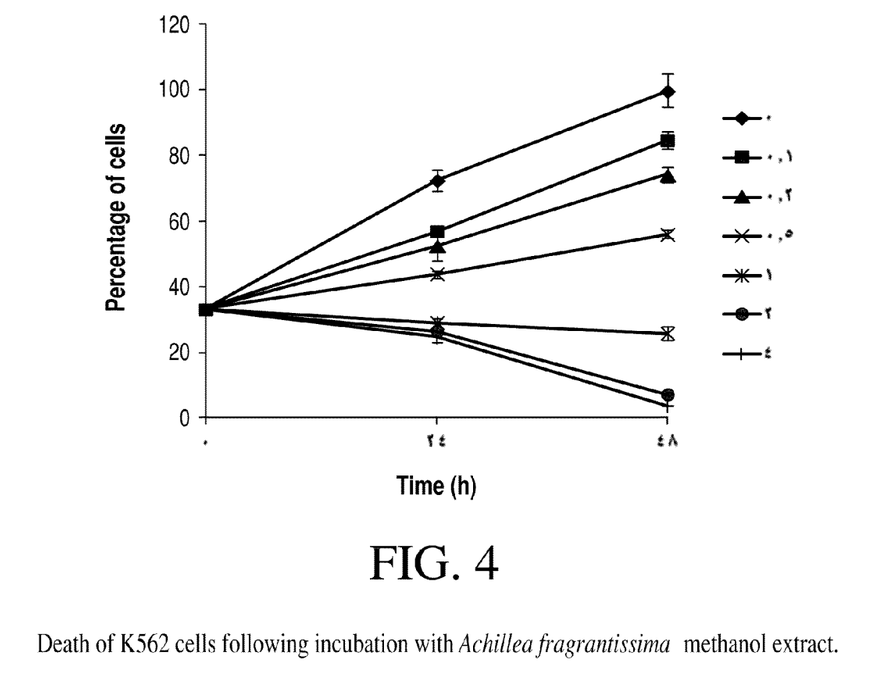
FIG. 4 Death of K562 cells following incubation with *Achillea fragrantissima* methanol extract; K562 cells incubated with increasing concentrations of *Achillea fragrantissima* extract, given in mg/ml of RPMI media, were followed for 48 h for cell growth. Viable cells were determined by trypan blue assay. Cell numbers with SD were averaged from 3 independent experiments. Cell death occurred at concentrations above 1 mg/mL of *Achillea fragrantissima* extract. Number of untreated cells at the end of the incubation period was considered 100%.
Figure 5A:
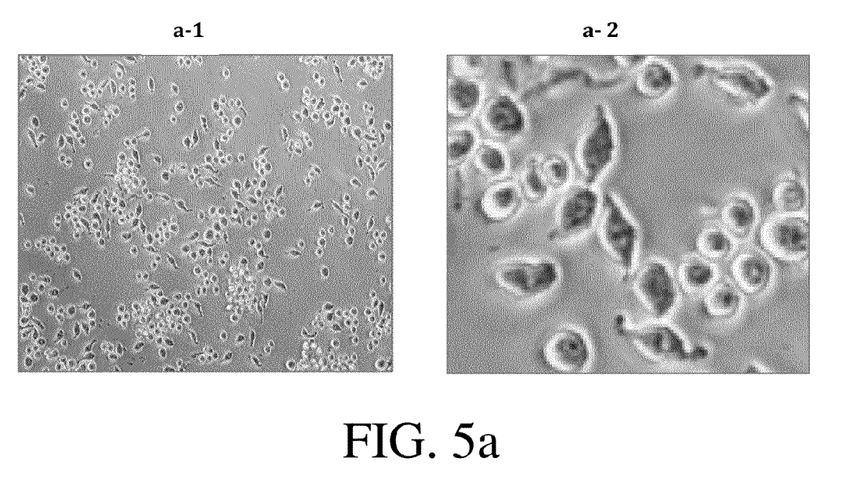
FIG. 5*a* shows the effect of compound (P1) of *Achillea fragrantissima* ether extract; a-1: An image of morphological change in K562 cells for compound P1; a-2: An enlarged image of morphological change in K562 cells for compound P1.
Figure 5B:
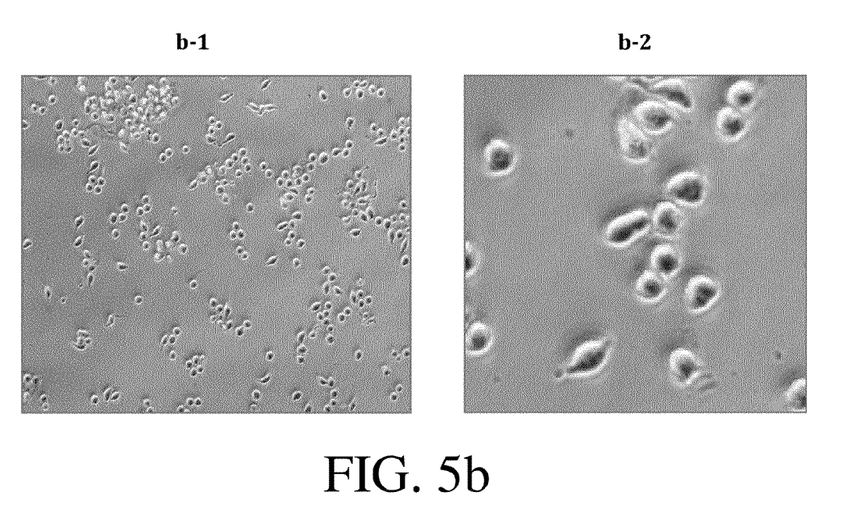
FIG. 5*b* shows the effect of compound (P2) of *Achillea fragrantissima* ether extract; b-1: An image of morphological change in K562 cells for compound P2; b-2: An enlarged image of morphological change in K562 cells for compound P2.
Figure 5C:
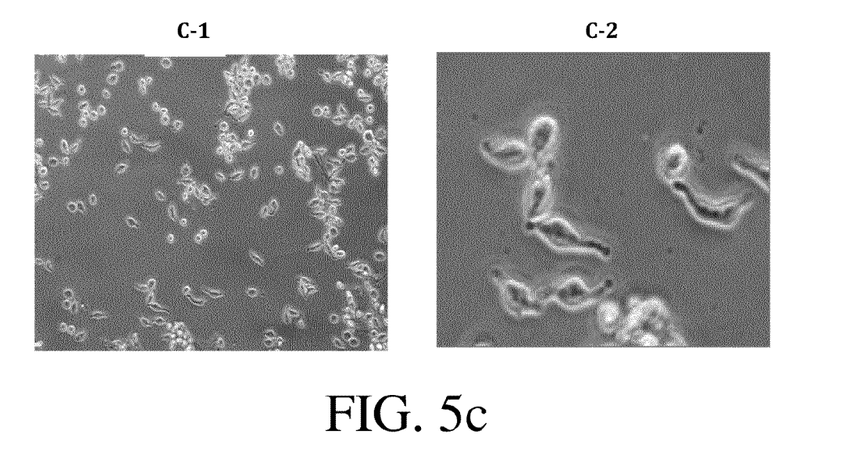
FIG. 5*c* shows the effect of compound (P3) isolated from *Achillea fragrantissima* ether extract; C-1: An image of morphological change in K562 cells for compound P3; C-2: An enlarged image of morphological change in K562 cells for compound P3.
Figure 5D:
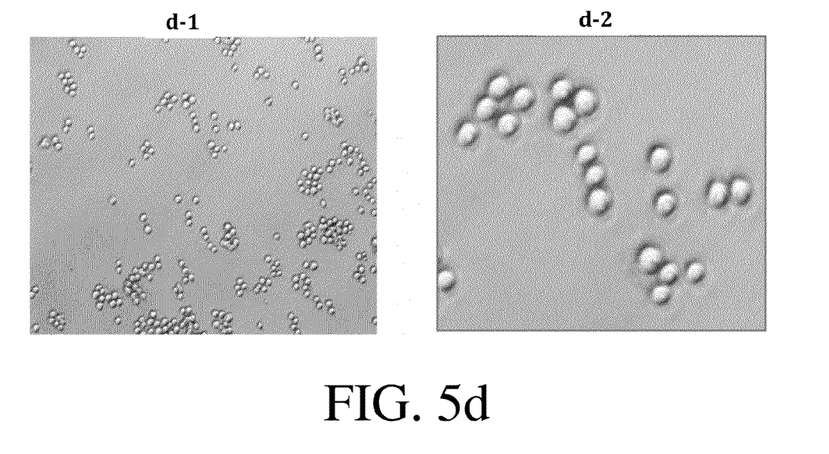
FIG. 5*d* shows the effect compound (P4) isolated from *Achillea fragrantissima* ether extract; d-1: An image of morphological change in K562 cells for compound P4, which seemed no change; d-2: An enlarged image of morphological change in K562 cells for compound P4
Figure 5E:
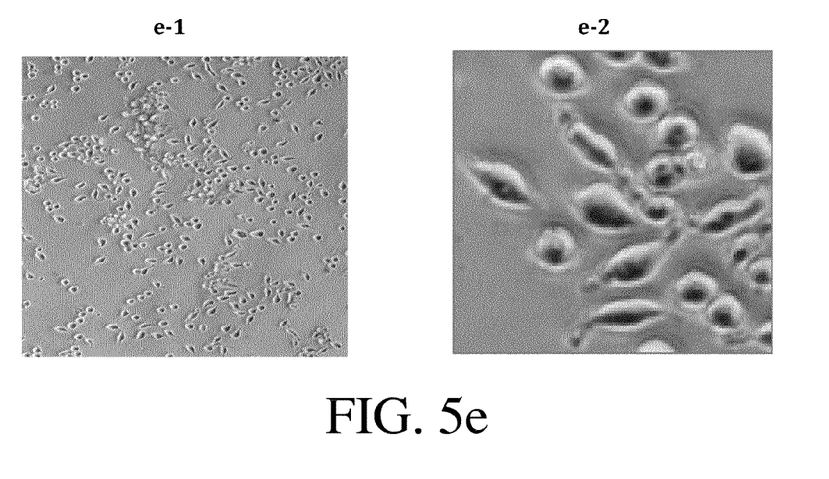
FIG. 5*e* shows the effect compound (P5) isolated from *Achillea fragrantissima* ether extract; e-1: An image of morphological change in K562 cells for compound P5; e-2: An enlarged image of morphological change in K562 cells for compound P5.
Figure 5F:
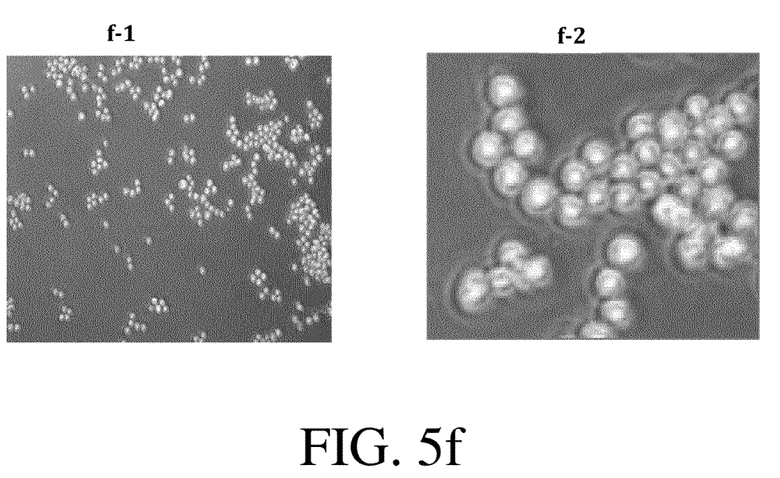
FIG. 5*f* is a K562 cells in RPMI medium as a Control; f-1: An image of control K562 cells; f-2: An enlarged image of control K562 cells.

FIG. 3. *Achillea fragrantissima* extract inhibits K562 cell proliferation. K562 cells incubated with 0.5 mg/mL of *Achillea fragrantissima* extract were followed for 72 h for cell growth. Viable cells were determined by trypan blue assay. *Achillea fragrantissima* extract inhibited the proliferation completely while the control cells grew exponentially during this period. Cell numbers with SD were averaged from 3 independent experiments. Number of untreated cells at the end of the incubation period was considered 100%.

FIG. 4. Death of K562 cells following incubation with *Achillea fragrantissima* extract. K562 cells incubated with increasing concentrations of *Achillea fragrantissima* extract, given in mg/mL of RPMI media, were followed for 48 h for cell growth. Viable cells were determined by trypan blue assay. Cell numbers with SD were averaged from 3 independent experiments. Cell death occurred at concentrations above 1 mg/mL of *Achillea fragrantissima* extract. Number of untreated cells at the end of the incubation period was considered 100%.

Biochemical Discussion

*Achillea fragrantissima* extracts have been shown to exhibit antiviral and anti-inflammatory properties. In this study, *Achillea fragrantissima* extract was found to induce differentiation in CML cell line K562 as indicated by clear morphological alterations from spherical to spindle shape and blebbing of the membrane. At low concentrations, *Achillea fragrantissima* extract blocked the proliferation of cells. At higher concentrations, *Achillea fragrantissima* extract caused membrane disintegration and death of K562 cells in a dose and time dependent manner. Findings indicate that *Achillea fragrantissima* plant extract may be a novel therapeutic agent by inducing terminal differentiation and death of CML cells.

Proliferation, differentiation, and apoptosis of normal hematopoietic cells are closely intertwined and under normal circumstances are carefully balanced. Induction of differentiation is associated with a loss of proliferative capacity, and cell death accompanies hematopoietic cell maturation. Leukemic transformations can be related to dysregulation of each of these processes. Considerable evidence supports the notion that leukemias are likely to arise from the disruption of the differentiation process of hematopoietic progenitors (17).

The mechanism underlying the death of K562 cells caused by an extract from *A. fragrantissima* could be explained by the intermediate morphological changes. The morphological change in K562 cells from spherical to spindle shape, typically induced by 12-O-tetradecanoylphorbol-13-acetate (TPA) or phorbol 12-myristate 13-acetate (PMA), has been shown to be a reliable indicator of differentiation (18) (19). In Applicant's study, a higher proportion of spindle shaped cells, found at lower concentration of *Achillea fragrantissima* extract, indicate differentiation as an intermediate stage before final death of the cells. At higher concentration, *fragrantissima* extract induced apoptosis was more prominent as seen from the number of K562 cells with disintegrating plasma membrane.

K562 cell death by apoptosis following differentiation has been reported for several plant components (20) (21). Blebbing of the plasma membrane of K562 cells was used as an indicator of membrane disintegration and apoptosis and has been described previously (21-23).

Several disadvantages have been seen in the application of chemotherapeutic agents and small molecule tyrosine kinase inhibitors directed against specific kinases in the treatment of cancers. These include development of drug resistance and unavoidable non-specific toxicities. Differentiation therapy is a potentially less toxic approach to treating cancers implemented by employing agents that induce cancer cell differentiation and terminal cell division which eventually lead to apoptosis. Differentiation therapy is now beginning to show translational promise in the clinical setting (24) (25).

Also, unlike targeted therapies, phytotoxic agents have been shown to act by inhibiting multiple pathways that underlie complex diseases like cancer, mostly through their antioxidant functions, and rarely result in drug resistance (26). *Achillea fragrantissima* has been shown to be a powerful inhibitor of lipopolysaccharide (LPS) induced nitric oxide (NO) synthesis and various proinflammatory mediators like IL-1$\beta$, TNF-$\alpha$, MMP-9, COX-2 and iNOS (13). Out of 65 plant extracts tested for various anti-inflammatory functions *A. fragrantissima* was found to be the most potent in inhibiting NO synthesis (13). *Achillea fragrantissima* has been shown to possess strong antioxidant potential (14) and may be the driving force underlying induction of differentiation and death of K562 cells. In this respect, *Achillea fragrantissima*, while promises to be a potential therapeutic agent in drug resistant CML also warrants further work in the treatment of other cancers.

The following experiment is described in 3 stages. The first stage is extraction, the second stage indicates a cell line experiment and a third stage defines a pharmacology experiment.

Part I
Plant Material and Extraction

Two kilograms of the aerial parts (branches, leaves and flowers), of the plant *Achillea fragrantissima* were washed under running tab water to remove dust, and then dried on absorbent paper to dry from washing water, left in the shade for a period of about 7 days in a dry airy place, at room temperature, then, reduced to powder.

The air-dried powdered herbs (1500 gm) of *Achillea fragrantissima* were extracted three times with MeOH (methyl alcohol) under reflux. The companied methanol extracts (about 5 liters) were evaporating under reduced pressure to dryness. The dried MeOH extract (430 gm.) was suspended in water (1 L.), and then fractionated with different solvents, diethylether, chloroform ($CHCl_3$), ethylacetate (EtOAc) and normal butanol (n-BuOH). Each fraction was evaporated under reduced pressure to dryness to yield the residues of diethylether fraction (21 g), $CHCl_3$ fraction (11 g), EtOAc fraction (13 g) and n-BuOH fraction (26 g).

Five compounds were isolated from ether extract using column chromatography (CC) and preparative chromatography (TLC) named as P1, P2, P3, P4 and P5. The structure of the isolated compounds was confirmed by spectroscopy means.

Part II
Effect of *Achillea fragrantissima* Methanol Extract on K562 Cell:
1. Materials for Biochemical Studies The cell culture medium (RPMI-1640), fetal bovine serum (FBS) and penicillin-streptomycin were purchased from Gibco BRL (Life technology). The K562 cell line derived originally from chronic myelogenous leukemia (CML) which is a genetic disorder in pluripotent stem cell that acquires Philadelphia (Ph) chromosome patient in blast crisis was obtained from American Type Culture Collection (ATCC), USA.

*Achillea fragrantissima* Extract Preparation.

One hundred mg of dried *Achillea fragrantissima* extract was redissolved in 200 ul of water to yield a solution with a final concentration of 0.5 mg/ml, centrifuged to remove any undissolved material and the supernatant used for treating cells.

Cell Culture

The human K562 cell line was cultured in RPMI-1640 medium supplemented with FBS (10%, v/v), streptomycin (100 µg/mL) and penicillin (100 U/mL). $5 \times 10^4$ cells/mL were distributed into 24 well plates (1 mL/well) and incubated under 5% $CO_2$ in a humidified atmosphere at 37° C. After 24 h of incubation, when the cells were ~20% confluent, appropriate concentrations of *Achillea fragrantissima* extracts and HPLC fractions from *Achillea fragrantissima* were added from the aqueous stock solution of 0.5 mg/ml. Incubations were continued for various durations and at the end cells were counted by trypan blue method.

Cell Viability Assay

Cell numbers and viabilities were assessed using a hemocytometer based on the ability of the viable cells to exclude trypan blue.

Morphological Evaluation of Differentiated Cells

Pictures of *Achillea fragrantissima* treated and control cells were taken after 24 h using inverted light microscope. Differentiated K562 cells were identified on the basis of morphological changes.

2. Biochemical Analysis Results
Effect of *Achillea fragrantissima* Methanol Extract on K562 Cell Morphology

*Achillea fragrantissima* methanol extract was added at various concentrations into cells grown in RPMI medium containing 10% FBS and penicillin and streptomycin antibiotics. Initial studies revealed significant morphological changes in K562 cells and hence further studies were pursued with these cells.

*Achillea fragrantissima* methanol extract altered the morphology of K562 cells. The effect was more pronounced at 0.5 mg/ml concentration. Morphological changes involve alteration from the original spherical to elliptical shapes (FIG. 1). At concentration of 1 mg/ml cells were more elongated and seem to indicate cell cycle arrest (FIG. 2). At concentration >1 mg/ml disintegration of membrane and cell death seems to predominate rather than shape change. Up to 30% of cells were morphologically altered at 16 h after addition of *Achillea fragrantissima* methanol extract. The morphological changes were found to be good predicators of future cell death.

Effect of *Achillea fragrantissima* Methanol Extract on Cell Viability

*Achillea fragrantissima* extract induced death of K562 cells in a dose- and time-dependent manner. At a low concentration of 0.5 mg/ml *Achillea fragrantissima* extract inhibited the cell growth while the control cells grew exponentially in our observations over a 3 day period (FIG. 3). *Achillea fra-*

*grantissima* extract inhibited growth from 0.1 mg/ml concentration and level of inhibition increased with increasing concentration of the extract (FIG. 4). From concentrations above 1 mg/ml death of cells was seen just after 24 h. Death of most of the cells occurred at 48 h at 2 and 4 mg/ml concentrations.

Part III
Pharmacology Experiment:
Materials and Methods
Plant Material

Two kilograms of the aerial parts of *Achillea* were collected, identified then dried and reduced to course powder. The air-dried powdered herbs (1500 gm) of *Achillea fragrantissima* were extracted three times with MeOH (methyl alcohol) under reflux. The companied methanol extracts (about 5 liters) were evaporating under reduced pressure to dryness. The dried MeOH extract (430 gm.) was suspended in water (1 L.), and then fractionated with different solvents, diethylether, chloroform ($CHCl_3$), ethylacetate (EtOAc) and normal butanol (n-BuOH). Each fraction was evaporated under reduced pressure to dryness to yield the residues of diethylether fraction (21 g), $CHCl_3$ fraction (11 g), EtOAc fraction (13 g) and n-BuOH fraction (26 g).

Five compounds were isolated from ether extract using column chromatography (CC) and preparative chromatography (TLC) named as P1, P2, P3, P4 and P5. The structure of the isolated compounds was confirmed by spectroscopy means.

Animals

Male Waster rats (220-230 g) were used. Rats were maintained in cages with raised floors of wide wire mesh to prevent coprophagy. All animals were kept under uniform and controlled conditions of temperature and light/dark (12/12 h) cycles. The animals were fed with standard pelleted diet and water ad libitum and were left one week for acclimatization to animal room condition.

Preparation of the Tested Extracts and Compounds:

A known weight of total methanol extract and each of the isolated compounds (P1-P5) and the reference drug (TKIs) was dissolved in 3% v/v Tween 80 to produce solutions of 10% concentration.

Doses:

In absence of $LD_{50}$ values for the total methanol extract and each of the isolated compounds, an experimental dose of 100/mg kg was selected in this investigation to be given orally to rats. The reference drug, TKIs, were given orally at a certain dose (30 mg/kg). This dose was calculated by converting the therapeutic dose that used in human to rat's dose according to the table of Paget & Barnes (1964).

Determination of $LD_{50}$ $LD_{50}$ of methanol extract and the isolated compounds were estimated in albino mice (25-30 g) according to the method of Finney (1964). In a preliminary test, animals in groups of three, received one of 100, 500, 1000, 2000, or 4000 mg/kg of the methanol extract and compounds by the oral route Animals were observed for 24 h for signs of toxicity and number of deaths. From the results of the first test, doses in between the minimal dose that kills all mice as well as the maximal dose that fails to kill any animal were chosen and given orally to fresh groups of mice. Control animals were received the vehicle and kept under the same conditions without any treatments. Signs of toxicity and number of deaths per dose in 24 h were recorded and the $LD_{50}$ of the tested compounds was calculated as the geometric mean of the dose that resulted in 100% mortality and that which caused no lethality at all.

Measurement of Liver and Kidney Function Markers:

Liver functions were evaluated by measuring the serum activity of alanine aminotransferase (ALT) and aspartate aminotransferase (AST) following the method of Reitman and Frankel (1957). Serum levels of total bilirubin (Walter and Gerarade, 1970), total proteins (Henary et al., 1974) and albumin (Doumas et al., 1971) were also assayed. Serum concentrations of urea (Wills and Savory, 1981) and creatinine (Kroll et al., 1987) were determined colormetrically as measures of kidney functions.

Induction of Leukemia K562 Cell in Rats:

The anti-cancer activity of TKIs and the methanol extract of *Achillea fragrantissima* and the isolated compounds, were carried out according to the method described by Ratajczak et al. (1992).

Rats were divided into 8 equal groups. The $1^{st}$ and $2^{nd}$ groups were received the vehicle only (10 ml/kg) and kept as normal control and K562 control groups, respectively. Animals in the $3^{rd}$ group (reference) were given TKIs (30 mg/kg). Other groups were administered methanol extract and the isolated compounds in a dose of 100 mg/Kg. All medications were administered orally via a stainless steel intubation needle. All animals were injected intraperitoneally with cyclophosphamide [150/mg kg, total dose, =3 mg] on each of two successive days. Twenty-four hours after the second injection, animals were transplanted by tail vein injection with $1 \times 10^7$ K562 human leukemia cells, that had been washed and seeded into fresh medium [RPMI 1640 medium/10% (vol/vol) fetal bovine serum] 12 h prior to use. After transplantation of the K562 cells, animals were monitored for the presence of circulating blast cells by blood sampling from the retro-orbital plexus according to Ratajczak et al. (1992) method.

After 5 weeks, leukemic cell transplantation in animals was monitored for the development of overt leukemia by retro-orbital plexus bleeding thrice weekly. When the peripheral-blood blast-cell content was at least 1-5% of the total leukocyte count, as determined by a 200-cell differential count in a standard hemocytometer chamber, treatment was initiated.

Two doses of TKIs, the methanol extract and the isolated compounds were given in the first day at 8:00 and 16:00 O' clock and a third dose was given on the second day, 1.5 h before blood sampling from the retroorbital plexus.

TKIs: Imatinib mesylate is the active component of Gleevec. Imatinib mesylate is designated chemically as 4-[(4-methyl-1-piperazinyl)methyl]-N-[4-methyl-3-[[4-(3-pyridinyl)-2-pyrimidinyl]aminophenyl]benzamide methanesulfonate.

Statistical Analysis

Statistical significance of survival differences among animals in the various oligomer treatment groups was determined, Result and Discussion:
Determination of $LD_{50}$ All rats treated with different doses of the total methanol extract of *Achillea fragrantissima* and each of the isolated compounds (up to 4000 mg/kg) were survive during the 24 h of observation.

The animals did not show visible signs of acute toxicity, therefore it suggested that the oral $LD_{50}$ of each of the tested compounds was higher than 4/g kg. The tested compounds are considered to be highly safe since substances possessing $LD_{50}$ higher than 50 mg/kg are non toxic (Buck et al; 1976). Effect of the Total Methanol Extract and the Isolated Compounds of *Achillea fragrantissima* on Animals:

After K562 cell transplantation, animals were monitored for circulating blast cells by retroorbital plexus blood sampling. Blast cells were demonstrable in peripheral blood within 5-6 weeks. They were morphologically distinguished from mouse leukocytes by their large size. Blast cell measurements (n=50) revealed a diameter of =28 μm, in comparison to =8 μm for the mouse leukocytes.

Shortly after manifesting peripheral leukemia, the animals became weak and sickly in appearance. Neurologic manifestations were a prominent part of the clinical picture. Limb paresis, circling gait, and other manifestations of central nervous system (CNS) disease including marked bulging of the cranium from hydrocephalus developed in 100% of the control animals ($2^{ed.}$ group).

On the other hand, once circulating leukemic blast cells had been detected, the survival of untreated control rat was 6+/−3 days (mean+/−SD). The survival of animals treated for 7 to 14 days with TKIs was not statistically different from the control animals. In distinct contrast, animals treated for similar lengths of time with plant extract and isolated compounds survived at least 5 times longer than the various control animals. In addition, animals receiving plant extract and/or isolated compounds had significantly less side effects most frequently, manifesting leukemic cell infiltration, and the central nervous system and others. These results suggest that *Achillea fragrantissima* methanolic extract and isolated compounds may be efficacious for the treatment of human leukemia in vivo, and by analogy, for the treatment of other human neoplasias.

The results of these experiments provide clear evidence that methanol extract and the isolated compounds of *Achillea fragrantissima* have significant single-agent anti leukemic activity in an in vivo model. The simplest and perhaps most compelling evidence in support of this statement is that we were able to significantly prolong the life of animals with established leukemia with sequence dependent.

Treatment was not initiated until the onset of measurable disease to obtain an accurate assessment of our plant activity in a clinically relevant model.

Because of the safety of this plant, and because the lack of sophisticated capabilities to proceed in this research, we have been do agreement with "King Faisal Specialist Hospital and Research Center" to work on the expansion of this research and further clinical treatment on volunteers.

Summary

Extract from *Achillea fragrantissima*, a herbal plant with known anti-inflammatory and antiviral properties, induced differentiation of CML cell line K652 leading to terminal cell division and cell death. Due to its non-toxic nature, extract of *Achillea fragrantissima* may serve as a CML therapeutic agent in patients resistant to tyrosine kinase inhibitors.

Test was only on human cells, but not on the human body to know whether her disadvantages side was gradual doses from low to high on these cells. But this plant does not have any toxic effects definitively as mentioned in all sources and references.

While the invention has been disclosed in connection with its preferred embodiments it should be recognized that changes and modifications may be made therein without departing from the scope of the claims.

What is claimed is:

1. A method for inhibiting the growth and promoting the mortality of chronic myeloid leukemia in a mammal in need thereof using an *Achillea fragrantissima* extract preparation, said method comprising the following steps:
    a) providing a mass of *Achillea fragrantissima* leaves and washing said leaves to remove dirt;
    b) drying the washed leaves at room temperature for seven days and powdering the dried leaves;
    c) extracting 1 kg of the powdered leaves with methanol three times under reflux;
    d) concentrating the methanol extract in a rotary evaporator under reduced pressure at 35° C. over anhydrous sodium sulfate;
    e) dissolving about 100 mg of the concentrated extract in 200 uL of water to form a solution;
    f) centrifuging the solution to remove any undissolved material therefrom to obtain said *Achillea fragrantissima* extract preparation; and
    g) administering to said mammal an effective amount of a pharmaceutical composition consisting essentially of said *Achillea fragrantissima* extract preparation.

2. A method for inhibiting the growth and promoting the mortality of chronic myeloid leukemia in a mammal in need thereof using an *Achillea fragrantissima* extract preparation, said method comprising the following steps:
    a) providing a mass of *Achillea fragrantissima* leaves and washing said leaves to remove dirt;
    b) drying the washed leaves at room temperature for seven days and powdering the dried leaves;
    c) extracting 1 kg of the powdered leaves with methanol three times under reflux;
    d) concentrating the methanol extract in a rotary evaporator under reduced pressure at 35° C. over anhydrous sodium sulfate;
    e) dissolving about 100 mg of the concentrated extract in 200 uL of water to form a solution;
    f) centrifuging the solution to remove any undissolved material therefrom to obtain said *Achillea fragrantissima* extract preparation;
    g) providing a sample of chronic myeloid leukemia cells and introducing said cells into a Roswell Park Memorial Institute (RPMI 1640) culture media supplemented with 10% v/v fetal bovine serum, streptomycin (100~g/mL) and penicillin (100 UmL);
    h) distributing $5 \times 10^4$ cells/ml into 24 well plates (1 ml/well), adding an amount of said *Achillea fragrantissima* extract preparation to the well plates, then incubating the well plates under 5% $CO_2$ in a humidified atmosphere at 37° C.;
    i) evaluating cell mortality 16 hours after the addition of said *Achillea fragrantissima* extract preparation to determine a suitable dosage for administering to said mammal; and
    j) administering to said mammal an effective amount of a pharmaceutical composition consisting essentially of said *Achillea fragrantissima* extract preparation.

3. The method according to claim 1, further comprising the step of determining an initial dosage of said *Achillea fragrantissima* extract preparation for administering to a human being with chronic myeloid leukemia, prior to the step of administering.

4. The method according to claim 2, wherein said *Achillea fragrantissima* extract preparation is administered in combination with streptomycin (100 μg/mL) and penicillin (100 UmL).

5. The method according to claim 4, wherein the mammal is a human being.

6. The method according to claim 5, wherein said composition is administered to the human being through oral, intravenous, intramuscular or subcutaneous routes.

7. The method according to claim 6, wherein said composition is administered through intravenous injection.

8. A method for inhibiting the growth and promoting the mortality of chronic myeloid leukemia in a mammal in need thereof using an *Achillea fragrantissima* extract preparation, said method consisting of:

a) providing a mass of *Achillea fragrantissima* leaves and washing said leaves to remove dirt;
b) drying the washed leaves at room temperature for seven days and powdering the dried leaves;
c) extracting 1 kg of the powdered leaves with methanol three times under reflux;
d) concentrating the methanol extract in a rotary evaporator under reduced pressure at 35° C. over anhydrous sodium sulfate;
e) dissolving about 100 mg of the concentrated extract in 200 uL of water to form a solution;
f) centrifuging the solution to remove any undissolved material therefrom to obtain said *Achillea fragrantissima* extract preparation; and
g) determining a suitable dosage for administering to a human being with chronic myeloid leukemia: and
h) administering an effective amount of a pharmaceutical composition consisting essentially of said *Achillea fragrantissima* extract preparation.

* * * * *